United States Patent [19]

Morozumi et al.

[11] Patent Number: 4,668,778
[45] Date of Patent: May 26, 1987

[54] NUCLEOSIDE 5'-ALKYL- OR ALKENYLPHOSPHATE

[75] Inventors: Manami Morozumi, Choshi; Shinji Sakata, Sagamihara, both of Japan

[73] Assignee: Yamasa Shoyu Kabushiki Kaisha, Chiba, Japan

[21] Appl. No.: 729,905

[22] Filed: May 3, 1985

Related U.S. Application Data

[63] Continuation of Ser. No. 505,252, Jun. 17, 1983, abandoned.

[30] Foreign Application Priority Data

Jun. 23, 1982 [JP] Japan ................. 57-108084

[51] Int. Cl.$^4$ ............................................ C07H 19/20
[52] U.S. Cl. ........................................ 536/27; 536/28; 536/29
[58] Field of Search .................. 536/26, 28, 29, 27

[56] References Cited

U.S. PATENT DOCUMENTS

| | | | |
|---|---|---|---|
| 3,336,289 | 8/1967 | Wechter et al. | 536/27 |
| 3,466,273 | 9/1969 | Sowa et al. | 536/27 |
| 4,093,714 | 6/1978 | Tolman et al. | 424/180 |
| 4,123,609 | 10/1978 | Behnke et al. | 536/27 |
| 4,211,773 | 7/1980 | Lopez et al. | 424/180 |
| 4,230,698 | 10/1980 | Bobek et al. | 424/180 |
| 4,239,905 | 12/1980 | Kodama et al. | 536/29 |
| 4,344,937 | 8/1982 | Machida | 424/180 |
| 4,357,324 | 11/1982 | Montgomery et al. | 424/180 |
| 4,367,332 | 1/1983 | Nishimura et al. | 536/23 |
| 4,386,076 | 5/1983 | Machida et al. | 424/180 |

FOREIGN PATENT DOCUMENTS

| | | | |
|---|---|---|---|
| 2025419 | 1/1980 | United Kingdom | 19/10 |
| 2108964 | 5/1983 | United Kingdom | 19/4 |

OTHER PUBLICATIONS

Mian et al., Synthesis and Biological Activity of 9-B-D-Arabinofuranosyladenine Cyclic 3',5'-Phosphate and 9-B-D-Arabinofuranosylguanine Cyclic 3',5'-Phosphate, J. Medicinal Chem., 17, 259 (1974).
Chemical Abstracts 86: 30033f (1977).
Chemical Abstracts 88: 23342u (1978).

*Primary Examiner*—Johnnie R. Brown
*Attorney, Agent, or Firm*—Wenderoth, Lind & Ponack

[57] ABSTRACT

Nucleoside 5'-alkyl- or alkenyl phosphate compounds represented by the following formula [I]

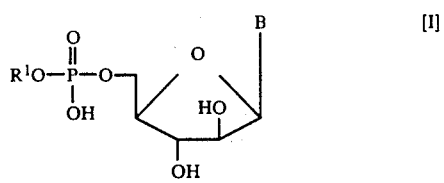

wherein B is a purine base having a substituent or a 5-substituted uracil base, and $R^1$ is an alkyl or alkenyl group having 14 to 26 carbon atoms, and pharmaceutically acceptable salts thereof are novel derivatives of arabinonucleosides which can have properties suitable for clinical application as antiviral agents, particularly for treating viral hepatitis.

2 Claims, No Drawings

NUCLEOSIDE 5'-ALKYL- OR ALKENYLPHOSPHATE

This application is a continuation of application Ser. No. 505,252, filed June 17, 1983, now abandoned.

BACKGROUND OF THE INVENTION

The present invention relates to nucleoside 5'-alkyl- or alkenylphosphates which are novel derivatives of nucleosides having antiviral activity.

9-β-D-Arabinofuranosylpurine and 1-β-D-arabinofuranosylpyrimidine and their derivatives are known to exhibit high antiviral activity, and the commercial production of some of these compounds in the form of antiviral agents has been under development in recent years. Most of the data on the antiviral activity of arabinonucleosides heretofore reported has mainly related to the activity, for example, against herpes-simplex virus which is a DNA virus. Recently, 9-β-D-arabinofuranosyladenine has been reported to have activity against hepetitis virus, and other arabinonucleosides are expected to become effective remedies for viral hepatitis.

SUMMARY OF THE INVENTION

The present invention has been accomplished with a view to providing novel arabinonucleoside derivatives which have properties suitable for clinical application as antiviral agents and particularly for treating viral hepatitis.

More specifically, the present invention relates to nucleoside 5'-alkyl- or alkenylphosphates represented by the formula [I]:

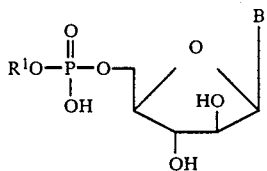

wherein B is a purine base having a substituent or a 5-substituted uracil base, and $R^1$ is an alkyl or alkenyl group having 14 to 26 carbon atoms and pharmaceutically acceptable salts thereof.

The compound of the present invention is an arabinonucleoside derivative which possesses antiviral activity and can be absorbed readily through the alimentary canal. It can also exhibit such a specific distribution to the liver and lasting pharmacological effect that the compound is metabolized in the liver to form an intermediate metabolite which accumulates and remains for a relatively long period of time, the intermediate metabolite being further metabolized slowly to release an arabinonucleoside. This compound is expected to be an effective drug especially for viral diseases including viral hepatitis.

DETAILED DESCRIPTION OF THE INVENTION

The purine base with a substituent, which is designated as B in the formula [I] set forth above, is represented by the following formula [II]:

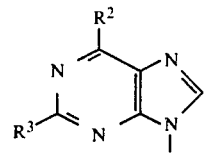

In formula [II], $R^2$ is an amino, hydroxyl or mercapto group, and $R^3$ is a hydrogen atom, or a hydroxyl or, amino group.

Examples of the purine bases represented by the formula [II] are adenine, guanine, isoguanine, hypoxanthine, 2,6-diaminopurine, 6-thioguanine, and 6-mercaptopurine.

Further, the 5-substituted uracil base, which is also designated as B in the formula [I], is represented by the following formula [III]:

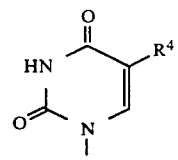

In the above formula, $R^4$ is a lower alkyl, lower alkenyl, or halogenoalkenyl group.

Examples of the 5-substituted uracil bases represented by the formula [III] are thymine, 5-ethyluracil, 5-vinyluracil, 5-propenyluracil, 5-(2-halogenovinyl)uracil such as 5-(2-bromovinyl)uracil, 5-(2-chlorovinyl)uracil and 5-(2-iodovinyl)uracil, and 5-(3,3,3-trifluoropropenyl)uracil.

$R^1$ in the formula [I], on the other hand, is an alkyl or alkenyl group having 14 to 26 carbon atoms such as, for example, tetradecyl, pentadecyl, cetyl, heptadecyl, stearyl, nonadecyl, eicosyl, heneicosyl, tricosyl, hexacosyl, oleyl, linoleyl, and linolenyl.

The present invention encompasses all of the compounds of the formula [I] in which B and $R^1$ are defined as above, and further includes pharmaceutically acceptable salts thereof. Examples of such salts are alkali metal salts such as sodium, potassium and lithium salts, alkaline earth metal salts such as calcium and magnesium salts, and ammonium salts.

The process for preparing the compound of this invention is not particularly limited, by any chemical process suitable for the purpose can be employed. A most common process comprises condensing arabinonucleoside-5'-monophosphate with an alcohol corresponding to the species of the alkyl or alkenyl group in the desired compound in an organic solvent in the presence of a condensing agent.

The arabinonucleoside-5'-monophosphate used in this process as a starting compound is a known compound or can be easily prepared by chemical or enzymatic 5'-position phosphorylation of an arabinonucleoside. In order to increase the stability of the arabinonucleoside-5'-monophosphate in the solvent, it is preferable that this compound be used in the form of a salt or that a protective group be introduced into the reactive functional group which can be contained in the base moiety of the arabinose moiety of the arabinonucleoside-5'-monophosphate, for example, the hydroxyl or amino group.

Examples of the salts are tertiary alkylammonium salts (such as triethylammonium salt, tri-n-butylammonium salt, and tri-n-octylammonium salt), quaternary alkylammonium salts (such as methyl-tri-n-butylammonium salt and methyl-tri-n-octylammonium salt), and amidine salts (such as 4-morpholine-N,N'-dicyclohexylcarboxyamidine salt), while examples of the protective groups are acyl groups (such as acetyl, propionyl, butyryl and benzoyl groups).

For the solvent to be used in the reaction, any organic solvent that does not adversely affect the reaction may be employed, and such a solvent can be suitably selected depending upon the species of the arabinonucleoside-5'-monophosphate, alcohol and condensing agent. For instance, the solvent may be one of N,N'-dimethylformamide, N,N'-dimethylacetamide, pyridine, dioxane, tetrahydrofuran, ethyl acetate, and tri-n-butylamine, or may be selected from mixtures comprising two or more of these solvents.

The species of the alcohol to be condensed with the arabinonucleoside-5'-monophosphate is selected according to the species of the alkyl or alkenyl residue of the desired compound. More particularly, any alcohol selected from tetradecanol, pentadecanol, cetyl alcohol, heptadecanol, stearyl alcohol, nonadecanol, eicosanol, heneicosanol, tricosanol, hexacosanol, oleyl alcohol, linoleyl alcohol, and linolenyl alcohol may be employed.

For the condensing agent, arylsulfonyl chlorides may be used. Examples of suitable chlorides are triisopropylbenzenesulfonyl chloride, o-toluenesulfonyl chloride, tosyl chloride, benzenesulfonyl chloride, and mesitylenesulfonyl chloride.

The ratio of the starting compounds and reaction conditions in the condensation reaction can be determined appropriately. For example, a suitable molar ratio among the arabinonucleoside-5'-monophosphate, alcohol and condensing agent is 1:1 to 6:1 to 6. The reaction temperature ranges from room temperature to about 100° C., and the reaction time is ordinarily 1 to 24 hours.

The desired compound thus obtained can be isolated from the reaction solution by a conventional method. For instance, the isolation can be carried out by suitably selecting and combining known purification processes such as liquid-liquid extraction, ion-exchange chromatography, adsorption chromatography, and recrystallization.

In order to indicate more fully the nature of this invention, the following specific examples of practice showing the compounds of the present invention and the processes for preparation thereof are set forth, it being understood that these examples are presented as illustrative only and are not intended to limit the scope of the invention.

EXAMPLE 1

Ten (10) mmol of $N^6,O^{2'},O^{3'}$-triacetyl-9-$\beta$-D-arabinofuranosyladenine-5'-monophosphate (tri-n-butylamine salt) was dissolved in 30 mmol of cetyl alcohol and 50 ml of pyridine. To the solution obtained was added 20 mmol of tosyl chloride, and the resulting solution was caused to react overnight at room temperature.

Water and chloroform were added to the reaction solution, which was then stirred. A layer of chloroform was formed and was isolated, and aqueous ammonia and ethanol were added thereto to deacetylate the product After completion of the reaction, water was added and the mixture was stirred. An aqueous layer was formed and was isolated, and hydrochloric acid was added thereto to adjust the pH of the solution to 1.0. A precipitate was formed and was separated by filtration. To this precipitate was added water, and the pH of the mixture was adjusted to 7.0 with sodium hydroxide to obtain a solution. The pH of the solution thus obtained was adjusted to 1.0 with hydrochloric acid to form a precipitate. The precipitate formed was separated by filtration. To the precipitate was added ethanol, and the mixture was stirred. Thereafter, the precipitate was separated by filtration and dried to obtain 3.6 g of 9-$\beta$-D-arabinofuranosyladenine-5'-cetyl phosphate.

Melting point (decomposition): 195° C.

Ultraviolet absorption: $\lambda_{max}$ (pH 7.0): 259 nm. $E_1\ cm^{1\%}$ (259 nm, pH 7.0): 226. $OD_{250}/OD_{260}$: 0.84. $OD_{280}/OD_{260}$: 0.24.

Elementary analysis: Found: C, 53.22, H, 8.14, N, 11.59. Calculated for $C_{26}H_{46}N_5O_7P.H_2O$: C, 52.96, H, 8.20, N, 11.88.

EXAMPLE 2

The procedure of Example 1 was followed except that the cetyl alcohol was replaced by stearyl alcohol, whereby 4.0 g of 9-$\beta$-D-arabinofuranosyladenine-5'-stearyl phosphate was obtained.

Melting point (Decomposition): 180° C.

Ultraviolet absorption: $\lambda_{max}$ (pH 7.0): 259 nm. $E_1\ cm^{1\%}$ (259 nm, pH 7.0): 217. $OD_{250}/OD_{260}$: 0.80. $OD_{280}/OD_{260}$: 0.26.

Elementary analysis: Found: C, 54.66, H, 8.55, N, 11.08. Calculated for $C_{28}H_{50}N_5O_7P.H_2O$: C, 54.44, H, 8.48, N, 11.34.

EXAMPLE 3

The procedure of Example 1 was followed except that the cetyl alcohol was replaced by eicosanol, whereby 3.7 g of 9-$\beta$-D-arabinofuranosyladenine-5'-eicosyl phosphate was obtained.

Melting point (Decomposition): 178° C.

Ultraviolet absorption: $\lambda_{max}$ (pH 7.0): 259 nm. $E_1\ cm^{1\%}$ (259 nm, pH 7.0): 201. $OD_{250}/OD_{260}$: 0.80. $OD_{280}/OD_{260}$: 0.28.

Elementary analysis: Found: C, 55.81, H, 8.74, N, 10.61. Calculated for $C_{30}H_{54}N_5O_7P.H_2O$: C, 55.80, H, 8.74, N, 10.84.

EXAMPLE 4

The procedure of Example 1 was repeated except that the cetyl alcohol was replaced by oleyl alcohol, whereby 1.6 g of 9-$\beta$-D-arabinofuranosyladenine-5'-oleyl phosphate was obtained.

Melting point (Decomposition): 178° C.

Ultraviolet absorption: $\lambda_{max}$ (pH 7.0) 259 nm. $E_1\ cm^{1\%}$ (259 nm, pH 7.0): 207. $OD_{250}/OD_{260}$: 0.87. $OD_{280}/OD_{260}$: 0.25.

Elementary analysis: Found: C, 55,51, H, 8.27, N, 11.61. Calculated for $C_{28}H_{48}N_5O_7P.\frac{1}{2}H_2O$: C, 55.43, H, 8.14, N, 11.54.

EXAMPLE 5

Ten (10) mmol of $O^{2'}$, $O^{3'}$-diacetyl-1-$\beta$-D-arabinofuranosylthymine-5'-monophosphate (tri-n-butylamine salt) was dissolved in 30 mmol of stearyl alcohol and 50 ml of pyridine. To the solution obtained was added 20 mmol of triisopropylbenzenesulfonyl chloride, and the resulting solution was caused to react overnight at room temperature.

Water and chloroform were added to the reaction solution, which was then stirred. A layer of chloroform was formed and was isolated, and aqueous ammonia and ethanol were added thereto to deacetylate the product. After deacetylation the reaction solution was concentrated to dryness, which was again dissolved in chloroform. The chloroform solution thus obtained was adsorbed on silica gel (300 g) packed in a column. Through the column were passed 2 l each of a 10:1 mixture of chloroform and methanol and a 5:1 mixture of chloroform and methanol, and then elution was conducted with 3 l of a 2:1 mixture of chloroform and methanol. The eluate was concentrated to dryness, dissolved in water, and adjusted to a pH of 1.0 with hydrochloric acid. A precipitate was formed and was prepared by filtration and recrystallized from ethanol to obtain 3.9 g of 1-$\beta$-D-arabinosylthymine-5'-stearyl phosphate.

Melting point (Decomposition): 170° C.

Ultraviolet absorption $\lambda_{max}$ (pH 7.0): 268 nm. $E_{1\ cm}^{1\%}$ (268 nm): 144. $OD_{250}/OD_{260}$: 0.60. $OD_{280}/OD_{260}$: 0.86.

Elementary analysis: Found: C, 57.13, H, 8.94, N, 4.62. Calculated for $C_{28}H_{51}N_2O_9P$: C, 56.93, H, 8.70, N, 4.74.

EXAMPLE 6

A reaction was carried out similarly as in Example 5 except that the stearyl alcohol was replaced by olelyl alcohol. The chloroform solution was subjected to a silica gel column chromatography. The eluate was concentrated to dryness, dissolved in water, and adjusted to a pH of 1.0 with hydrochloric acid. A precipitate was formed and was separated by filtration and recrystallized from water to obtain 1.8 g of 1-$\beta$-D-arabinofuranosylthymine-5'-oleyl phosphate.

Melting point (Decomposition): 173° C.

Ultraviolet absorption: $\lambda_{max}$ (pH 7.0): 268 nm. $E_{1\ cm}^{1\%}$ (268 nm): 150. $OD_{250}/OD_{260}$: 0.60. $OD_{280}/OD_{260}$: 0.93.

Elementary analysis: Found: C, 57.33, H, 8.56, N, 4.49. Calculated for $C_{28}H_{49}N_2O_9P$: C, 57.13, H, 8.39, N, 4.76.

EXAMPLE 7

The procedure of Example 5 was followed except that the $O^{2'},O^{3'}$-diacetyl-1-$\beta$-D-arabinofuranosylthymine-5'-monophosphate (tri-n-butylamine salt) was replaced by $O^{2'},O^{3'}$-diacetyl-1-$\beta$-D-arabinofuranosyl-E-5-(2-bromovinyl)uracil-5'-monophosphate (tri-n-butylamine salt). As a result, 2.6 g of 1-$\beta$-D-arabinofuranosyl-E-5-(2-bromovinyl)uracil-5'-stearyl phosphate was obtained.

Melting point (Decomposition): 166° C.

Ultraviolet absorption: $\lambda_{max}$ (pH 7.0): 253, 296 nm. $E_{1\ cm}^{1\%}$ (253 nm): 196, (296 nm): 154. $OD_{250}/OD_{260}$: 1.12. $OD_{280}/OD_{260}$: 0.69.

Elementary analysis: Found: C, 50.89, H, 7.40, N, 3.83. Calculated for $C_{29}H_{50}N_2O_9PBr$: C, 51.10, H, 7.39, N, 4.11.

EXAMPLE 8

The procedure of Example 6 was repeated except that the $O^{2'},O^{3'}$-diacetyl-1-$\beta$-D-arabinofuranosylthymine-5'-monophosphate (tri-n-butylamine salt) was replaced by $O^{2'},O^{3'}$-diacetyl-1-$\beta$-D-arabinofuranosyl-E-5-(2-bromovinyl)uracil-5'-monophosphate (tri-n-butylamine salt), whereby 2.3 g of 1-$\beta$-D-arabinofuranosyl-E-5-(2-bromovinyl)uracil-5'-oleyl phosphate was obtained.

Melting point (Decomposition): 164° C.

Ultraviolet absorption: $\lambda_{max}$ (pH 7.0): 253, 296 nm. $E_{1\ cm}^{1\%}$ (253 nm): 189, (296 nm): 149. $OD_{250}/OD_{260}$: 1.14. $OD_{280}/OD_{260}$: 0.70.

Elementary analysis: Found: C, 51.31, H, 7.41, N, 3.70. Calculated for $C_{29}H_{48}N_2O_9PBr$: C, 51.25, H, 7.12, N, 4.12.

EXAMPLE 9

By repeating the procedure of Example 1 except that cetyl alcohol is replaced with linoleyl alcohol or with linolenyl alcohol, 9-$\beta$-D-arabinofuranosyladenine-5'-linoleyl phosphate or 9-$\beta$-D-arabinofuranosyladenine-5'-linolenyl phosphate is produced, respectively.

We claim:

1. Nucleoside 5'-alkyl- or alkenylphosphate represented by the formula:

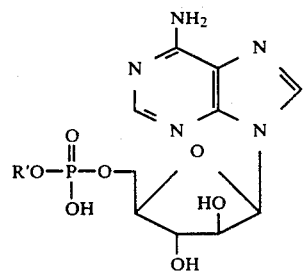

wherein $R^1$ is an alkyl or alkenyl group having 14 to 26 carbon atoms; and pharmaceutically acceptable salts thereof.

2. The compound as claimed in claim 1 wherein $R^1$ is an alkyl or alkenyl group having 16 to 20 carbon atoms.

* * * * *